United States Patent

Krämer et al.

[11] 4,215,131
[45] Jul. 29, 1980

[54] ANTIMICROBIAL AGENTS

[75] Inventors: Wolfgang Krämer; Karl H. Büchel; Manfred Plempel; Ingo Haller, all of Wuppertal, Fed. Rep. of Germany

[73] Assignee: Bayer Aktiengesellschaft, Leverkusen, Fed. Rep. of Germany

[21] Appl. No.: 21,295

[22] Filed: Mar. 16, 1979

Related U.S. Application Data

[63] Continuation-in-part of Ser. No. 819,645, Jul. 27, 1977, abandoned.

[30] Foreign Application Priority Data

Aug. 7, 1976 [DE] Fed. Rep. of Germany ....... 2635665

[51] Int. Cl.$^2$ .......................... A01N 9/00; A01N 9/22
[52] U.S. Cl. ............................ 424/273 R; 424/232; 424/269
[58] Field of Search .................... 260/308 R; 424/269, 424/273, 232; 548/341

[56] References Cited

U.S. PATENT DOCUMENTS

| | | | |
|---|---|---|---|
| 3,796,704 | 3/1974 | Metzger et al. | 260/309 |
| 3,812,142 | 5/1974 | Meiser et al. | 548/341 |
| 3,952,002 | 4/1976 | Kramer et al. | 260/308 A |
| 4,005,083 | 1/1977 | Buchel et al. | 424/273 |
| 4,038,404 | 7/1977 | Meiser et al. | 424/269 |
| 4,154,842 | 5/1979 | Kramer et al. | 424/269 |

Primary Examiner—Allen J. Robinson
Attorney, Agent, or Firm—Sprung, Felfe, Horn, Lynch & Kramer

[57] ABSTRACT

Pharmaceutical compositions free from pathogenic microorganisms which could be harmful to warm-blooded animals, are provided containing, as an active ingredient, an antimicrobially effective amount of at least one compound of the formula

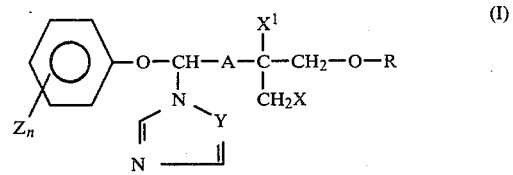

in which
R represents hydrogen, —CO—$R^1$ or —$SO_2$—$R^2$, wherein
$R^1$ represents optionally substituted alkyl, alkenyl or alkinyl, optionally substituted phenyl, optionally substituted phenoxyalkyl, phenylalkyl, cycloalkyl, alkylamino, dialkylamino or optionally substituted phenylamino,
$R^2$ represents alkyl or optionally substituted phenyl,
A represents a keto group or a —CH(OH)— grouping,
X represents hydrogen or an —OR grouping, wherein
R is as defined above,
$X^1$ represents alkyl or optionally substituted phenyl,
Y represents —CH— or a nitrogen atom,
Z represents halogen, alkyl, halogenoalkyl, cycloalkyl, alkoxy, alkylthio, alkoxycarbonyl, optionally substituted phenyl, optionally substituted phenoxy, optionally substituted phenylalkyl, amino, cyano or nitro and
n represents 0 or an integer from 1 to 5, or a salt thereof, in admixture with a sterile pharmaceutical carrier, such as a solid or liquefied gaseous diluent, or with a liquid diluent other than a solvent of molecular weight less than 200 (preferably 300) except in the presence of a surface-active agent.

The compositions of the invention are useful as antimycotic agents.

Also included in the invention is the provision of the compositions of the invention in unit dosage form as well as the provision of methods of treatment wherein the compositions of the invention are administered to warm-blooded animals.

6 Claims, No Drawings

ANTIMICROBIAL AGENTS

This application is a continuation-in-part of application Ser. No. 819,645, filed July 27, 1977 now abandoned.

The present invention relates to the use of new 1-azolyl-4-hydroxy-butane derivatives as antimicrobial agents, in particular as antimycotic agents for warm-blooded animals.

It has already been disclosed that 3,3-dimethyl-1-(imidazol-1-yl)-1-phenoxy-butan-2-ones and -ols and 3,3-dimethyl-1-phenoxy-1-(triazol-1-yl)-butan-2-ones and -ols have a good antimycotic action (compare, respectively, German Offenlegungsschriften 2,105,490 and 2,333,355, and 2,247,186 and 2,324,424). However, their action, in particular against dermatophytes and in vivo against Candida, is not always completely satisfactory.

According to the present invention, there are provided pharmaceutical compositions free from pathogenic microorganisms which could be harmful to warm-blooded animals, containing as an active ingredient, at least one 1-azolyl-4-hydroxy-butane derivative of the formula

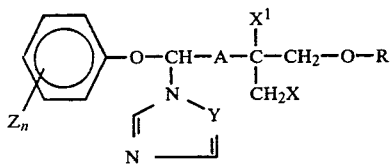

in which

R represents hydrogen, —CO—$R^1$ or —$SO_2$—$R^2$, wherein $R^1$ represents optionally substituted alkyl, alkenyl, alkinyl, optionally substituted phenyl, optionally substituted phenoxyalkyl, optionally substituted phenylalkyl, cycloalkyl, alkylamino, dialkyl-amino or optionally substituted phenylamino and $R^2$ represents alkyl or optionally substituted phenyl, A represents a keto group or a —CH(OH)— grouping, X represents hydrogen or an —OR grouping, wherein R is as defined above, $X^1$ represents alkyl or optionally substituted phenyl, Y represents —CH— or a nitrogen atom, Z represents halogen, alkyl, halogenoalkyl, cycloalkyl, alkoxy, alkylthio, alkoxycarbonyl, optionally substituted phenyl, optionally substituted phenoxy, optionally substituted phenylalkyl, amino, cyano or nitro and n represents 0 or an integer of from 1 to 5, or a salt thereof, in admixture with a sterile pharmaceutical carrier, such as a solid or liquefied gaseous diluent, or with a liquid diluent other than a solvent of molecular weight less than 200 (preferably 300) except in the presence of a surface-active agent.

Those compounds of the formula (I) in which A represents the CH(OH) group possess two asymmetric carbon atoms; they can thus exist in the two geometric isomers (erythro form and threo form), which can be obtained in various proportions. In both cases they exist as optical isomers. The formulae appearing in this specification are therefore to be construed as including the optical isomers of the compounds in pure form as well as racemates thereof. The isolation of the optical isomers is achieved by conventional techniques.

Surprisingly, the 1-azolyl-4-hydroxy-butane derivatives which can be used according to the invention exhibit a better antimycotic, therapeutically usable activity than the known 3,3-dimethyl-1-(imidazol-1-yl)-1-phenoxy-butan-2-ones and -ols and 3,3-dimethyl-1-phenoxy-1-(triazol-1-yl)-butan-2-ones and -ols, which are the most closely related compounds chemically and from the point of view of their action.

In the formula (I), $R^1$ preferably represents straight-chain or branches alkyl with 1 to 18 carbon atoms, which can be optionally substituted by halogen, amino, acetylamino alkoxy with 1 to 4 carbon atoms or alkoxycarbonyl with 1 to 4 carbon atoms in the alkyl part; and also, preferably, alkenyl and alkinyl with 2 to 6 carbon atoms in each case and cycloalkyl with 5 to 7 carbon atoms. In addition, $R^1$ preferably represents optionally substituted phenyl and phenylalkyl and phenoxyalkyl which have, in each case, 1 to 4 carbon atoms in the alkyl part and which are optionally substituted in the phenyl part, possible substituents being, preferably; halogen, amino, cyano, nitro or alkyl with 1 to 2 carbon atoms. furthermore, $R^1$ preferably represents alkylamino and dialkylamino with 1 to 4 carbon atoms in each alkyl part and optionally substituted phenylamino with, preferably, halogen, nitro and cyano as substituents. $R^2$ preferably represents straightchain or branched alkyl with 1 to 4 carbon atoms and optionally substituted phenyl, possible substituents being, preferably: halogen, amino, cyano, nitro or alkyl with 1 to 2 carbon atoms. $X^1$ preferably represents alkyl with 1 or 2 carbon atoms or phenyl which is optionally substituted by halogen, especially fluorine, chlorine or bromine, or alkyl with 1 to 2 carbon atoms. Z preferably represents halogen, straight-chain or branched alkyl with 1 to 4 carbon atoms, cycloalkyl with 5 to 7 carbon atoms, such as, in particular, cyclohexyl; furthermore, preferably, halogenoalkyl, such as perhalogenoalkyl and more specifically perfluoro or perchloro alkyl with 1 or 2 carbon atoms and 1 to 5 halogen atoms, such as, in particular, fluorine and chlorine atoms, and the trifluoromethyl group may be mentioned as an example; alkoxy and alkylthio with 1 or 2 carbon atoms in each case or alkoxycarbonyl with 1 to 5 carbon atoms; and furthermore, preferably, amino, cyano and nitro. In addition, Z preferably represents optionally substituted phenyl and phenoxy, possible substituents being, preferably: halogen, amino, cyano, nitro or alkyl with 1 to 2 carbon atoms; and finally also, preferably, substituted phenylalkyl with 1 or 2 carbon atoms in the alkyl part, a possible substituent in the alkyl part which should be mentioned being, preferably, alkylcarbonyl with a total of up to 3 carbon atoms and possible substituents in the phenyl part which should be mentioned being, preferably, halogen, especially fluorine, chlorine, bromine and iodine, nitro and cyano. The index n preferably represents 0 or integers from 1 to 3, and X and Y have the meaning indicated in the definition of the invention.

Examples of particularly active representatives of the active compounds according to the invention which may be mentioned are, in addition to the preparation examples and the examples in Table 1, the following: 4-acetoxy-1-(2-cyclohexylphenoxy)-3,3-dimethyl-1-(1,2,4-triazol-1-yl)-butan-2-one and -ol, 4-acetoxy-1-(2-cyclohexylphenoxy)-3,3-dimethyl-1-(imidazol-1-yl)-butan-2-one and -ol, 4-chloroacetoxy-1-(4-chlorophenoxy)-3,3-dimethyl-1-(1,2,4-triazol-1-yl)-butan-2-one and -ol, 4-chloroacetoxy-1-(4-chlorophenoxy)-3,3-dimethyl-1-(imidazol-1-yl)-butan-2-one and -ol, 1-[4-(4'-chlorophenyl)phenoxy]-3,3-dimethyl-4-methylcarbamoyloxy-1-(1,2,4-triazol-1-yl)-butan-2-one and -ol, 1-[4-(4'-chlorophenyl)-phenoxy]3,3-dimethyl-1-(imidazol-1-yl)-4-methylcarbamoyloxy-butan-2-one and -ol, 1-(4-chlorophenoxy)-3,3-dimethyl-4-hydroxy-1-(1,2,4-triazol-1-yl)-butan-2 one and -ol, 1-(4-chlorophenoxy)3,3-dimethyl-4-hydroxy-1-(imidazol-1-yl)-butan-2-one and -ol, 4-acetoxy-1-(4-chlorophenoxy)-3,3-dimethyl-1-(1,2,4-triazol-1-yl)-butan-2-ol, 4-acetoxy-1-(4-chlorophenoxy)-3,3-dimethyl-1-(imidazol-1-yl)-butan-2-ol, 1-(4-chlorophenoxy)-3,3-dimethyl-4-phenylcarbamoyloxy-1(1,2,4-triazol-1-yl-butan-1-one and -ol, 1-(4-chlorophenoxy)-3,3-dimethyl-1-(imidazol-1-yl)-4-phenylcarbamoyloxy-butan-2-one and -ol, 1-(4-chlorophenoxy)-3,3-dimethyl-4-(hexa-2,4-diethylcarbonyloxy)-1,2,4-(triazol-1-yl)-butan-2-one and -ol, 1-(4-chlorophenoxy)-3,3-dimethyl-4-(hexa-2,4-diethylcarbonyloxy)-1-(imidazol-1-yl-butan-2-one and -ol, 4-ethylcarbonyloxy-1-(4-chlorophenoxy)-3,3-dimethyl-1-(1,2,4-triazol-1-yl)-butan-2-one and -ol, 4-ethylcarbonyloxy-1-(4-chlorophenoxy)-3,3-dimethyl-1-(imidazol-1-yl)-butan-2-one and -ol, 4-ethylcarbonyloxy-1-[4-(4'-chlorophenyl)phenoxy]-3,3-dimethyl-1-(imidazol-1-yl)-butan-2-one and -ol, 1-(4-chlorophenoxy)-3,3-dimethyl-4-propylcarbonyloxy-1-(1,2,4-triazol-1-yl)-butan-2-one and -ol, 1-(4-chlorophenoxy)-3,3-dimethyl-4-iso-propylcarbonyloxy-1-(1,2,4-triazol-1-yl)butan-2-one and -ol, 1-(4-chlorophenoxy)-3,3-dimethyl-4-isopropylcarbonyloxy-1-(imidazol-1-yl)-butan-2-one and -ol, 1-(4-chlorophenoxy)-3,3-dimethyl-4-pentylcarbonyloxy-1-(1,2,4-triazol-1-yl)-butan-2-one and -ol, 1-[4(4'-chlorophenyl)phenoxy]-3,3-dimethyl-1-(imidazol-1-yl)-4-pentacarbonyloxybutan-2-one and -ol, 1-(4-chlorophenoxy)-3,3-dimethyl-4-heptylcarbonyloxy-1-(1,2,4-triazol-1-yl)-butan-2-one and -ol, 1-[4-(4'-chlorophenyl)-phenoxy]-3,3-dimethyl-4-heptylcarbonyloxy-1-(imidazol-1-yl)-butan-2-one and -ol, 1-(4-chlorophenoxy)-3,3-dimethyl-4-nonylcarbonyloxy-1-(1,2,4-triazol-1-yl)-butan-2-one and -ol, 1-(4-chlorophenoxy)-3,3-dimethyl-1-(imidazol-1-yl)-4-nonylcarbonyloxy-butan-2-one and -ol, 1-(4-chlorophenoxy)-3,3-dimethyl-1-(1,2,4-triazol-1-yl)-4-undercanylcarbonyloxy-butan-2-one and -ol, 1-(4-chlorophenoxy)-3,3-dimethyl-1(1,2,4-triazol-1-yl)-4-tridecanylcarbonyloxy-butan-2-one and -ol, 1-[4-(4'-chlorophenyl)-phenoxy]-3,3-dimethyl-1-(imidazol-1-yl)-4-tridecabylcarbonyloxy-butan-2-one and -ol, 1-(4-chlorophenoxy)-3,3-dimethyl-4-heptadecanylcarbonyloxy-1-(1,2,4-triazol-1-yl)-butan-2-one and -ol, 1-(4-chlorophenoxy)-3,3-dimethyl-4-pivaloyloxy-1-(1,2,4-triazol-1-yl)-butan-2-one and -ol, 1-(4-chlorophenoxy)-3,3-dimethyl-1-(imidazol-1-yl)-4-pivaloyoxy-butan-2-one and -ol, 1-[4-(4'-chlorophenyl)-phenoxy]-3,3-dimethyl-1-(imidazol-1-yl)-4-pivaloyloxy-butan-2-ol, 4-benzoyloxy-1-(4-chlorophenoxy)-3,3-dimethyl-1-(1,2,4-triazol-1-yl)-butan-2-one and -ol, 4-(4-chlorobenzoyloxy)-1-(4-chlorophenoxy)-3,3-dimethyl-1-(1,2,4-triazol-1-yl)-butan-2-one and -ol, 4-(4-chlorobenzoyloxy)-1-(4-chlorophenoxy)-3,3-dimethyl-1-(imidazol-1-yl)-butan-2-one and -ol, 4-(4-chlorobenzoyloxy)-1-[4-(4'-chlorophenyl)-phenoxy]-3,3-dimethyl-1-(imidazol-1-yl)-butan-2-one and -ol, 4-benzylcarbonyloxy-1-(4-chlorophenoxy)-3,3-dimethyl-1-(1,2,4-triazol-1-yl)-butan-2-one and -ol, 1-(4-chlorophenoxy)-4-cyclohexylcarbonyloxy-3,3-dimethyl-1-(1,2,4-triazol-1-yl)-butan-2-one and -ol, 4-chloroacetoxy-1-(4-chlorophenoxy)-3,3-dimethyl-1-(1,2,4-triazol-1-yl)butan-2-one and -ol, 4-chloroacetoxy-1-(4-chlorophenoxy)-3,3-dimethyl-1-(imidazol-1-yl)-butan-2-one and -ol, 4-chloroacetoxy-1-[4-(4'-chlorophenoxy)-phenoxy]-3,3-dimethyl-1-(imidazol-1-yl)-butan-2-one and -ol, 1-(4-chlorophenoxy)-4-dichloroacetoxy-3,3-dimethyl-1-(1,2,4-triazol-1-yl)-butan-2-one and -ol, 1-(4-chlorophenoxy)-4-dichloroacetoxy-3,3-dimethyl-1-(imidazol-1-yl)butan-2-one and -ol, 4-(2-chloroethylcarbonyloxy)-1-(4-chlorophenoxy-3,3-dimethyl-1-(1,2,4-triazol-1-yl)-butan-2-one and -ol, 1-(4-chlorophenoxy)-4-(3-chloropropylcarbonyloxy)-3,3-dimethyl-1-(1,2,4-triazol-1-yl)-butan-2-one and -ol, 1-(4-chlorophenoxy)-3,3-dimethyl-4-(1-methylvinylcarbonyloxy)-1-(1,2,4-triazol-1-yl)-butan-2-one and -ol, 1-(4-chlorophenoxy)-3,3-dimethyl-1-(imidazol-1-yl)-4-(1-methylvinylcarbonyloxy)-butan-2-one and -ol, 1-[4-(4'-chlorophenyl)-phenoxy]-3,3-dimethyl-1-(imidazol-1-yl)-4-(1-methylvinylcarbonyloxy)-butan-2-one and -ol, 1-(4-chlorophenoxy)-3,3-dimethyl-4-(penta-1,3-diethylcarbonyloxy)-1-(1,2,4-triazol-1-yl)-butan-2-one and -ol, 1-(4-chlorophenoxy)-4-cyanoacetoxy-3,3-dimethyl-1-(1,2,4-triazol-1-yl)-butan-2-one and -ol, 1-[4-(4'-chlorophenyl)-phenoxy]-4-cyanoacetoxy-3,3-dimethyl-1-(imidazol-1-yl)-butan-2-one and -ol, 4-ethoxycarbonylmethylcarbonyloxy-1-(4-chlorophenoxy)-3,3-dimethyl-1-(1,2,4-triazol-1-yl)-butan-2-one and -ol, 4-ethoxymethylcarbonyloxy-1-(4-chlorophenoxy)-3,3-dimethyl-1-(1,2,4-triazol-1-yl)-butan-2-one-and -ol, 4-ethoxymethylcarbonyloxy-1-[4-(4'-chlorophenyl)-phenoxy]-3,3-dimethyl-1-(imidazol-1yl)-butan-2-one and -ol, 1-(4-chlorophenoxy)-4-(2,4-dichlorophenoxymethylcarbonyloxy)-3,3-dimethyl-1-(1,2,4-triazol-1-yl)-butan-2-one and -ol, 1-(4-chlorophenoxy)-4-(2,4-dichlorophenoxymethylcarbonyloxy)-3,3-dimethyl-1-(imidazol-1-yl)-butan-2-one and -ol, 1-[4(4'-chlorophenyl)phenoxy]-4-(2,4-dichlorophenoxymethylcarbonyloxy)-3,3-dimethyl-1-(imidazol-1-yl)-butan-2-one and -ol, 4-acetylaminomethylcarbonyloxy-1-(4-chlorophenoxy)-3,3-dimethyl-1-(1,2,4-triazol-1-yl)-butan-2-one and -ol, 4-acetylaminomethylcarbonyloxy-1-[4-(4'-chlorophenyl)-phenoxy]-3,3-dimethyl-1-(imidazol-1-yl)-butan-2-one and -ol, 1-(4-chlorophenoxy)-3,3-dimethyl-4-methylsulphonylcarbonyloxy-1-(1,2,4-triazol-1-yl)-butan-2-one and -ol, 1-(4-chlorophenoxy)-3,3-dimethyl-1-(imidazol-1-yl)-4-methylsulphonylcarbonyloxy-butan-2-one and -ol, 1-[4-(4'-chlorophenyl)-phenoxy]-3,3-dimethyl-1-(imidazol-1-yl)-4-methylsulphonylcarbonyloxy-butan-2-one and -ol, 1-(4-chlorophenoxy)-3,3-dimethyl-4-hexadecanylcarbonyloxy-1-(1,2,4-triazol-1-yl)-butan-2-one and -ol, 4-butylcarbonyloxy-1-(4-chlorophenoxy)-3,3-dimethyl-1-(1,2,4-triazol-1-yl)-butan-2-one and -ol, 4-(ethyl-methylacetoxy)-1-(4-chlorophenoxy)-3,3-dimethyl-1-(1,2,4-triazol-1-yl)-butan-2-one and -ol, 1-(4-chlorophenoxy)-4-iso-butylcarbonyloxy-3,3-dimethyl-1-(1,2,4-triazol-1-yl)-butan-2-one and -ol, 1-(4-chlorophenoxy)-3,3-dimethyl-4-methylcarbamoyloxy-1-(1,2,4-triazol-1-yl)-butan-2-one-and -ol, 1-(4-chlorophenoxy)-3,3-dimethyl-1-(imidazol-1-yl)-4-methylcarbamoyloxy-butan-2-one and -ol, 1-(4-chlorophenoxy)-3,3-dimethyl-4-phenylcarbamoyloxy-1-(1,2,4-triazol-1-yl)-butan-2-one and -ol, 1-[4-(4'-chlorophenyl)-phenoxy]-3,3-dimethyl-1-(imidazol-1-yl)-4-phenylcarbamoyloxy-butan-2-one and -ol, 4-ethylcarbamoyloxy-1-(4-chlorophenoxy)-3,3-dimethyl-1-(1,2,4-triazol-1-yl)-butan-2-one and -ol, 4-acetoxy-3-ethyl-1-(4-chlorophenoxy)-3-methyl-1-(1,2,4-triazol-1-yl)-butan-2-one and -ol, 4-acetoxy-1-(4-chlorophenoxy)-3-(4-chlorophenyl)-3-methyl-1-(1,2,4-triazol-1-yl)-butan-2-one and -ol and 4-acetoxy-3-acetoxymethyl-1-(4-chlorophenoxy)-3-(4-chlorophenyl)-1-(1,2,4-triazol-1-yl)-butan-2-one and -ol.

The active compounds to be used according to the invention and their salts have not yet been disclosed. They can be prepared according to German Application P 26356661 (Le A 17,324) corresponding to concurrently filed U.S. application Ser. No. 819,534 filed July 27, 1977 and now U.S. Pat. No. 4,154,842 issued May 15, 1979 by reacting 1-bromo-4-(R-oxy)-butan-2-ones of the formula

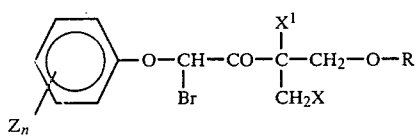

(II)

in which

R, X, $X^1$, Z and n have the meaning indicated above, with known azoles of the formula

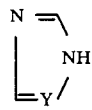

(III)

in which

Y has the meaning indicated above, by known methods in the presence of an inert organic solvent, for example acetone, and in the presence of an acid binding agent, for example potassium carbonate, at temperatures between 20° and 150° C., preferably between 60° and 120° C., and optionally selectively reducing the azolyl-ketones, obtained by this procedure, with complex borohydrides, for examples sodium borohydride, in a manner which is in itself known in the presence of a polar organic solvent, for example ethanol, at temperatures between 0° and 30° C. The isolation of the compounds of the formula (I) is carried out in a manner which is generally customary.

In some cases, it may be advantageous to "transesterify" individual compounds, starting from the 4-acetoxy-1-azolyl-1-phenoxy-butan-2-ones obtained according to the above process, via the corresponding 1-azolyl-4-hydroxy-1-phenoxy-butan-2-ones. For this, the 4-acetoxy-1-azolyl-1-phenoxybutan-2-ones are initially split hydrolytically with concentrated hydrochloric acid in the presence of a diluent. The 1-azolyl-4-hydroxy-1-phenoxybutan-2-ones formed by this procedure are then appropriately reacted with acid chlorides, isocyanates or sulphonyl chlorides in a manner which is generally known.

The 1-bromo-4-(R-oxy)-butan-2-ones of the formula (II) to be used as the starting materials can be prepared by known processes, for example by reacting a known phenol of the formula

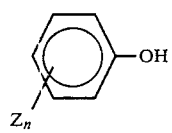

(IV)

in which

Z and n have the meaning indicated above, with a bromoketone of the formula

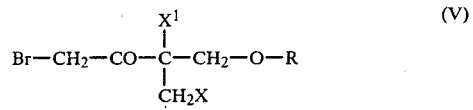

(V)

in which

R, X and $X^1$ have the meaning indicated above. The active hydrogen atom which still remains is then replaced by bromine in the customary manner (compare also the preparation examples).

The bromoketones of the formula (V) are generally known compounds in organic chemistry. They are obtained by reacting known ketones of the formula

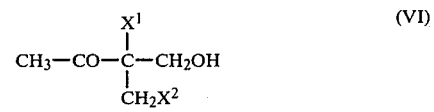

(VI)

in which $X^1$ has the meaning indicated above and $X^2$ represents hydrogen or hydroxyl, appropriately with acid chlorides, acid anhydrides, isocyanates or sulphonyl chlorides in a manner which is generally known. The active hydrogen atom which still remains is then replaced by bromine in the customary manner.

Preferred salts of the compounds of the formula (I) are the salts with physiologically acceptable acids. These include, preferably, the hydrogen halide acids, such as, for example, hydrochloric acid and hydrobromic acid, especially hydrochloric acid, phosphoric acid, nitric acid and monofunctional and bifunctional carboxylic acids and hydroxycarboxylic acids, such as, for example, acetic acid, maleic acid, succinic acid, fumaric acid, tartaric acid, salicyclic acid, citric acid, sorbic acid, pamoic acid and lactic acid, and 1,5-naphthalenedisulphonic acid.

The compounds of the formula (I) which can be used according to the invention, and their salts, show antimicrobial, in particular strong antimycotic, effects. They possess a very broad antimycotic spectrum of activity, especially against dermatophytes and blastomyces as well as biphase fungi, for example against species of Candida, such as Candida albicans, species of Epidermophyton, such as Epidermophyton floccosum, species of Aspergillus, such as Aspergillus niger and Aspergillus fumigatus, species of Trichophyton, such as Trichophyton mentagrophytes, species of Microsporon, such as Microsporon felineum and species of Penicillium, such as Penicillium commune. The recital of these micro-organisms in no way implies a limitation of the germs which can be combated but is only of illustrative character. The compounds of the formula (I) and their salts can be used in medicine. The term "pharmaceutical composition" includes compositions adapted for administration of warm-blooded animals. Such compositions are prepared free from pathogenic microorganisms which could be harmful to warm-blooded animals and include a sterile pharmaceutical carrier.

The following may be mentioned as examples of field of indication in medicine: dermatomycoses and systemic mycoses caused by Trichophyton mentagrophytes and other species of Trichophyton, species of Microsporon, Epidermophyton floccosum, blastomyces and biphase fungi as well as moulds.

The invention further provides a pharmaceutical composition containing as active ingredient a compound of the Formula (I) or a salt thereof in the form of a sterile or isotonic aqueous solution.

The invention also provides a medicament in dosage unit from comprising a compound of the formula (I) or a salt thereof.

The invention also provides a medicament in the form of tablets (including lozenges and granules), gragees, capsules, pills, ampoules or suppositories comprising a compound of the formula (I) or a salt thereof.

"Medicament" as used in this specification means physically discrete coherent portions suitable for medical administration. "Medicament in dosage unit form" as used in this specification means physically discrete coherent units suitable for medical administration each containing a daily dose or a multiple (up to four times) or sub-multiple (down to a fortieth) of a daily dose of the compound of the invention. Whether the medicament contains a daily dose or, for example, a half, a third, or a quarter of a daily dose will depend on whether the medicament is to be administered once or, for example, twice, three times or four times a day respectively.

The pharmaceutical compositions according to the invention may, for example, take the form of ointments, gels, pastes, creams, sprays (including aerosols), lotions, suspensions, solutions and emulsions of the active ingredient in aqueous or non-aqueous diluents, syrups, granules or pwders.

The diluents to be used in pharmaceutical compositions (e.g. granulates) adapted to be formed into tablets, dragees, capsules and pills include the following: (a) fillers and extenders, e.g. starch, sugars, mannitol, and silica acid; (b) binding agents, e.g. carboxymethyl cellulose and other cellulose derivatives, alginates, gelatine and polyvinyl pyrrolidone; (c) moisturizing agents, e.g. glycerol; (d) disintergrating agents, e.g. agar-agar, calcium carbonate and sodium bicarbonate; (e) agents for retarding dissolution e.g. paraffin; (f) resorption accelerators, e.g. quaternary ammonium compounds; (g) surface active agents, e.g. cetyl alcohol, glycerol monostearate; (h) adsorptive carriers, e.g. kaolin and bentonite; (i) lubricants, e.g. talc, calcium and magnesium stearate and solid polyethylene glycols.

The tablets, dragees, capsules and pills formed from the pharmaceutical compositions of the invention can have the customary coatings, envelopes and protective matrices, which may contain opacifiers. They can be so constituted that they release the active ingredient only or preferably in a particular part of the intestinal tract, possibly over a period of time. The coatings, envelopes and protective matrices may be made, for example, of polymeric substances or waxes.

The ingredient can also be made up in microencapsulated form together with one or several of the above-mentioned diluents.

The diluents to be used in pharmaceutical compositions adapted to be formed into suppositories can, for example, be the usual water-soluble or water-insoluble diluents, such as polyethylene glycols and fats (e.g. cocoa oil and high esters e.g. $C_{14}$-alcohol with $C_{16}$-fatty acid) or mixtures of these diluents.

The pharmaceutical compositions which are ointments, pastes, creams and gels can, for example, contain the usual diluents, e.g. animal and vegetable fats, waxes, paraffins, starch, tragacanth, cellulose derivatives, polyethylene glycols, silicones, bentonites, silicic acid, talc and zinc oxide or mixtures of these substances.

The pharmaceutical compositions which are powders and sprays can, for example, contain the usual diluents, e.g. lactose, talc, silicic acid, aluminium hydroxide, calcium silicate, and polyamide powder or mixtures or these substances. Aerosol sprays can, for example, contain the usual propellants, e.g. chlorofluorohydrocarbons.

The pharmaceutical compositions which are solutions and emulsions can, for example, contain the customary diluents (with, of course, the above-mentioned exclusion of solvents having a molecular weight below 200 except in the presence of a surface-active agent), such as solvents, dissolving agents and emulsifiers; specific examples of such diluents are water, ethyl alcohol, isopropyl alcohol, ethyl carbonate, ethyl acetate, benzyl alcohol, benzyl benzoate, propylene glycol, 1,3-butylene glycol, dimethylformamide, oils for example ground nut oil, glycerol, tetrahydrofurfuryl alcohol, polyethylene glycols and fatty acid esters of sorbitol or mixtures thereof.

For parenteral administration, the solutions and emulsions should be sterile, and, if appropriate, blood-isotonic.

The pharmaceutical compositions which are suspensions can contain the usual diluents, such as liquid diluents, e.g. water, ethyl alcohol, propylene glycol, surface-active agents (e.g. ethoxylated isostearyl alcohols, polyoxyethylene sorbite and sorbitane esters), microcrystalline cellulose, aluminium metahydroxide, bentonite, agar-agar and tragacanth or mixtures thereof.

All the pharmaceutical compositions according to the invention can also contain colouring agents and preservatives as well as perfumes and flavouring additions (e.g. peppermint oil and eucalyptus oil) and sweetening agents (e.g. saccharin).

The pharmaceutical compositions according to the invention preferably contain about 0.1 to 99.5, more preferably from about 0.5 to 95% of the active ingredient by weight of the total composition.

In addition to a compound of the invention, the pharmaceutical compositions and medicaments according to the invention can also contain other pharmaceutically active compounds. They may also contain a plurality of compounds of the invention.

Any diluent in the medicaments of the present invention may be any of those mentioned above in relation to the pharmaceutical compositions of the present invention. Such medicaments may include solvents of molecular weight less than 200 as sole diluent.

The discrete coherent portions constituting the medicament according to the invention will generally be adapted, by virtue of their shape or packaging, for medical administration and may be, for example, any of the following: tablets, (including lozenges and granules), pills, dragees, capsules, suppositories and ampoules. Some of these forms may be made up for delayed release of the active ingredient. Some, such as capsules, include a protective envelope which renders the portions of the medicament physically discrete and coherent.

The preferred daily dose for administration of the medicaments of the invention is 0.5 g to 30 g of active ingredient.

The production of the above-mentioned pharmaceutical compositions and medicaments is carried out by any method known in the art, for example, by mixing the active ingredient(s) with the diluent(s) to form a pharmaceutical composition (e.g. a granulate) and then forming the composition into the medicament (e.g. tablets).

This invention further provides a method of combating (including prevention, relief and cure of) the above-mentioned diseases in warm-blooded animals, which comprises administering to the animals a compound of the invention alone or in admixture with a diluent or in the form of a medicament according to the invention.

It is envisaged that these active compounds will be administered perorally, parenterally (for example intramuscularly, intraperitoneally or intravenously), rectally or locally, preferably parenterally, especially intravenously. Preferred pharmaceutical compositions and medicaments are therefore those adapted for parenteral, especially intravenous administration.

tioned amount of active compound must be exceeded. Any expert can easily decide the particular requisite optimum dosage and method of administration of the active compounds on the basis of his expert knowledge. The following examples illustrate the activity of the compounds used in the invention.

EXAMPLE A

Antimycotic in vitro activity

Description of the experiment:

The in vitro tests were carried out in a series dilution test with germ inocula of an average of $5 \times 10^4$ germs/ml of substrate. The nutrient medium was (a) for dermatophytes and moulds: Sabouraud's milieu d'epreuve and (b) for yeats: meat extract/glucose broth.

The incubation temperature was 28° C. and the duration of incubation was 24 to 96 hours.

Table A

| | Antimycotic in vitro activity | | | | |
|---|---|---|---|---|---|
| | Minimum inhibitory concentration values in mcg/ml of nutrient medium for | | | | |
| | Trichophyton mentagr. | Candida albicans | Penicillium commune | Aspergillus species | Microsporon felineum |
| Active Compound (known) [structure with C₂H₅, Cl, O—CH—CO—C(CH₃)₃, N, imidazole] | 40 | 64 | >100 | >100 | >100 |
| (known) [structure with Cl, Cl, O—CH—CO—C(CH₃)₃, N, triazole] | 40 | 64 | >100 | 100 | 100 |
| Compounds for example No: | | | | | |
| 2 | <1 | 64 | 64 | >64 | 32 |
| 3 | 0,25 | 64 | >64 | 64 | 8 |
| 4 | <1 | 64 | >64 | 64 | 64 |
| 8 | 8 | 32 | >64 | — | — |
| 13 | <1 | 64 | >64 | >64 | 32 |
| 14 | 4 | 64 | >64 | >64 | 32 |
| 15 | 8 | 32 | >64 | — | — |
| 16 | <1 | 64 | >64 | >64 | 64 |

In general it has proved advantageous in medicine, to administer the active compounds according to the invention in total amounts of about 10 to about 300, preferably 50 to 200 mg/kg of body weight every 24 hours, optionally in the form of several individual administrations, to achieve the desired results.

It can, however, be necessary to deviate from the dosages mentioned and in particular to do so as a function of the nature and the body weight of the subject to be treated, the nature and severity of the disease, the nature of the formulation and the administration of the medicament, and the time or interval at which administration takes place. Thus it can in some cases suffice to manage with less than the above mentioned amount of active compound whilst in other cases the above men-

EXAMPLE B

Antimycotic in vivo activity (oral) in candidosis of mice

Description of the experiment:

Mice of the type SPF-CF$_1$ were infected intravenously with $1-2 \times 10^6$ logarithmically growing Candida cells, which were suspended in physilogical sodium choloride solution. The animals were treated orally one hour before and seven hours after the infection with, in each case, 100 mg/kg of body weight of the formulations.

Untreated animals died from the infection 3 to 6 days after infection. The survival rate on the 6th day after infection was about 5% in the case of untreated control animals.

Table B

Antimycotic in vivo activity (oral) in *candidosis* of mice

| Active compound | Action |
|---|---|
| ![structure] C2H5, phenyl with Cl, O—CH—CO—C(CH3)3, triazole (known) | K.W. |
| Cl, Cl-phenyl, O—CH—CO—C(CH3)3, triazole (known) | + |
| Cl, Cl-phenyl, O—CH—CH(OH)—C(CH3)3, triazole (known) | K.W. |
| (CH3)3C-phenyl, O—CH—CH(OH)—C(CH3)3, triazole (known) | K.W. |

| Compound from Example No. | |
|---|---|
| 2 | + + + + |
| 3 | + + + + |
| 4 | + + + + |
| 13 | + + + |
| 14 | + + |

+ + + + + = very good action = 90% survivors on the 6th day after infection
+ + + + = good action = 80% survivors on the 6th day after infection
+ + + = action = 60% survivors on the 6th day after infection
+ + = poor action = 40% survivors on the 6th day after infection
+ = trace of action
K.W. = no action

EXAMPLE C

Antimycotic in vivo activity (local) using experimental trichophytosis of guinea pigs as a model Description of the experiment:

White guinea pigs of the Pirbright white strain were infected on the back, which has been shorn and not scarified, with a microconidia and macroconidia suspension of Trichophyton mentagrophytes. In the untreated animals, the typical picture of a dermatophytosis developed within 12 days after infection with reddening, scaling and loss of hair to the extent of total integumentary defect at the place of infection. The infected animals were treated locally, starting on the 3rd day after infection, once per day with 1% strength polyethylene glycol solutions of the formulation 2,3 and 4 according to the invention.

On the 14th day after infection, the untreated control animals showed the typical picture of a dermatophytosis, whilst the test formulations had completely inhibited the course of the infection. The following examples illustrate the preparations of individual compounds used in the invention.

EXAMPLE 1

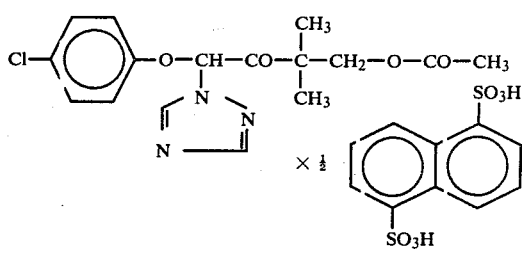

A solution of 36.3 g (0.2 mol) of crude 4-acetoxy-1-bromo-1-(4-chlorophenoxy)-3,3-dimethyl-butan-2-one in 50 ml of acetone is added dropwise to a suspension of 21 g (0.3 mol) of triazole and 30 g (0.2 mol) of potassium carbonate in 200 ml of acetone at the boil. After heating for 15 hours under reflux, the mixture is filtered and the filtrate is concentrated by distilling off the solvent in vacuo. The residue is taken up in 200 ml of methylene chloride and the methylene chloride solution is washed three times with 50 ml of water each time, dried over sodium sulphate and concentrated. The residue which remains is dissolved in 100 ml of acetone and 36 g (0.1 mol) of 1,5-naphthalenedisulphonic acid octahydrate in 100 ml of acetone are added. The crystalline precipitate which forms is filtered off and dried. This gives 45 g (45% of theory) of 4-acetoxy-1-(4-chloro-phenoxy)-3,3-dimethyl-1-(1,2,4-triazol-1-yl)-butan-2-one 1,5-naphthalenedisulphonate of melting point 155°–160° C.

PREPARATION OF THE STARTING MATERIAL.

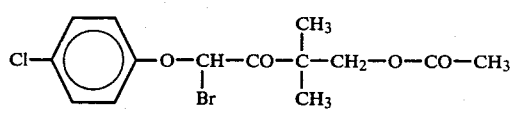

170 g (0.72 mol) of 4-acetoxy-1-bromo-3,3-dimethyl-butan-2-one in 200 ml of acetone are added dropwise to a suspension of 92.1 g (0.72 mol) of 4-chlorophenol and 108 g (0.72 mol) of potassium carbonate in 1,000 ml of acetone in the course of 100 minutes. After heating for 15 hours, whilst stirring and under reflux, the mixture is filtered and the filtrate is concentrated by distilling off the solvent in vacuo. The residue is taken up in 200 ml of methylene chloride and the methylene chloride solution is washed three times with 50 ml of water each time, dried over sodium sulphate and concentrated. The oily residue is distilled. This gives 153 g (72% of theory) of 4-acetoxy-1-(4-chloro-phenoxy)-3,3-dimethyl-butan-2-one of boiling point 140°–145° C./0.2 mm Hg.

56.9 g (0.2 mol) of 4-acetoxy-1-(4-chlorophenoxy) 3,3-dimethylbutan-2-ones are dissolved in 350 ml of carbon tetrachloride. 10.3 g (0.2 mol) of bromine are added dropwise at room temperature, so that steady consumption takes place. The mixture is then stirred for 30 minutes at room temperature. After distilling off the solvent in vacuo, 4-acetoxy-1-bromo-1-(4-chlorophenoxy)-3,3-dimethylbutan-2-one, which can be further reacted directly, is quantitatively obtained.

EXAMPLE 2

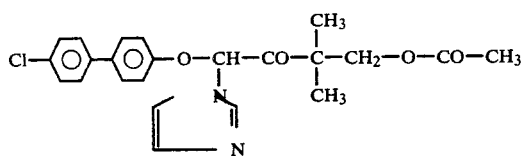

22 g (0.05 mol) of 4-acetoxy-1-bromo-1-[4-(4'-chlorophenyl)-phenoxy]-3,3-dimethyl-butan-2-one are dissolved in 20 ml of acetone and the solution is added dropwise to 5.5 g (0.08 mol) of imidazole and 7.5 g (0.05 mol) of potassium carbonate in 80 ml of acetone at the boil. After heating for 15 hours under reflux, the mixture is filtered and the filtrate is concentrated by distilling off the solvent in vacuo. The residual oil is washed with 50 ml of water and crystallised out and recrystallised in ether. This gives 9 g (42.2% of theory) of 4-acetoxy-1-4-(4'-chlorophenyl)phenoxy-3,3-dimethyl-1-(imidazol-1-yl)-butan-2-one of melting point 100°–112° C.

EXAMPLE 3

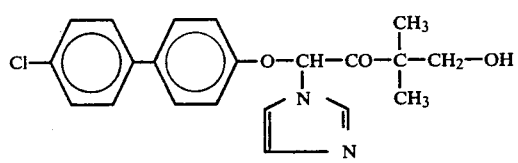

12 ml of concentrated hydrochloric acid are added to 42.8 g (0.1 mol) of 4-acetoxy-1-[4-(4'-chlorophenyl)-phenoxy]3,3-dimethyl-1-(imidazol-1-yl)-butan-2-one (example 2) in 200 ml of methanol and the mixture is heated for 8 hours under reflux. The solvent is then distilled off in vacuo and 50 ml of a saturated solution of sodium bicarbonate and 50 ml of pentane are added to the residue. After 2 hours, the crystalline product is filtered off. This gives 38.9 g (100% of theory) of 1-[4-(4'-chlorophenyl)-phenoxy]3,3dimethyl-4-hydroxy-1-(imidazol-1-yl)-butan-2-one of melting point 133°–135° C.

EXAMPLE 4

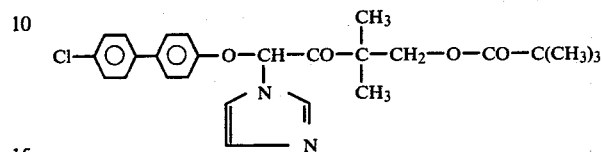

7.72 g (0.02 mol) of 1-[4-(4'-chlorophenyl)-phenoxy]3,3-dimethyl-4-hydroxy-1-(imidazol-1-yl)-butan-2-one (Example 3) are dissolved in 50 ml of methylene chloride, 5 ml of pivaloyl chloride are added and the mixture is heated for 5 hours under reflux. The solvent is then distilled off in vacuo, the residue is taken up in methylene chloride and the methylene chloride solution is washed twice with 50 ml of a saturated solution of sodium bicarbonate each time and concentrated. The residue is taken up in 50 ml of pentane, whereupon it crystallises. This gives 5.3 g (60% of theory) of 1-[4-(4'-chlorophenyl)-phenoxy]-3-,3-dimethyl-1-(imidazol-1-yl)-4-pivaloyloxybutan-2-one of melting point 98°–103° C.

The following examples of the general formula

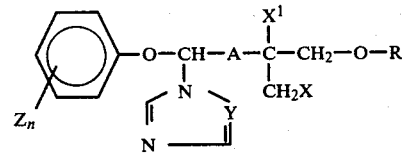

are obtained analogously to the abovementioned examples.

| Example No. | $Z_n$ | Y | A | X | $X^1$ | R | Melting point (°C.) |
|---|---|---|---|---|---|---|---|
| 5 | 4-NO$_2$ | N |  | H | CH$_3$ | —CO—CH$_3$ | 110–111 |
| 6 | 4-⌬ | N | CO | H | CH$_3$ | —CO—CH$_3$ | 113–114 |
| 7 | 4-⌬-Cl | N | CO | H | CH$_3$ | —CO—CH$_3$ | 114–115 |
| 8 | 2,4-Cl$_2$ | N | CO | H | CH$_3$ | —CO—CH$_3$ | Viscous oil |
| 9 | 2,4-Cl$_2$ | N | CO | H | CH$_3$ | —CO—CH$_3$ | 173–174 (× ½ naphthalene-1,5-disulfonic acid) |
| 10 | — | N | CO | H | CH$_3$ | —CO—CH$_3$ | viscous oil |
| 11 | 4-Cl | N | CO | —O—CO—CH$_3$ | CH$_3$ | —CO—CH$_3$ | 85–86 |
| 12 | 4-NO$_2$ | CH | CO | H | CH$_5$ | —CO—CH$_3$ | 148–151 |

-continued

| Example No. | $Z_n$ | Y | A | X | $X^1$ | R | Melting point (°C.) |
|---|---|---|---|---|---|---|---|
| 13 | 2,4-$Cl_2$ | CH | CO | H | $CH_3$ | —CO—$CH_3$ | 69–70 |
| 14 | 4-Cl | CH | CO | H | $CH_3$ | —CO—$CH_3$ | 72–74 |
| 15 | — | CH | CO | H | $CH_3$ | —CO—$CH_3$ | viscous oil |
| 16 | 4-$\bigcirc$-Cl | CH | CO | H | $CH_3$ | —CO—$(CH_2)_{16}$—$CH_3$ | 58–68 |
| 17 | 4-Cl | CH | CO | H | $CH_3$ | H | 104–105 |
| 18 | 4-Cl | N | CO | H | $CH_3$ | H | 110–111 |
| 19 | 4-$\bigcirc$-Cl | CH | CHOH | H | $CH_3$ | H | 138–143 |
| 20 | 4-Cl | CH | CO | H | $CH_3$ | —CO—$CHCl_2$ | 102–104 |
| 21 | 4-Cl | N | CHOH | H | $CH_3$ | H | 96–105 |
| 22 | 4-Cl | N | CO | H | $CH_3$ | —CO—$C_{11}H_{23}$ | Viscous oil |
| 23 | 4-Cl | N | CO | H | $CH_3$ | —CO—$CH_2Cl$ | 69 |
| 24 | 2,4-$Cl_2$ | N | CO | H | $CH_3$ | H | 104–110 |
| 25 | 4-Cl | N | CO | H | $CH_3$ | —CO—$C_5H_{11}$ | Viscous oil |
| 26 | 4-$\bigcirc$-Cl | CH | CO | H | $CH_3$ | —CO—$C_7H_{15}$ | 50–53 |
| 27 | 4-Cl | N | CO | H | $CH_3$ | —CO—$C_2H_5$ | 58–60 |
| 28 | 4-Cl | N | CO | H | $CH_3$ | —CO—$CHCl_2$ | 60–62 |
| 29 | 4-Cl | N | CO | H | $CH_3$ | —CO—$C_{17}H_{35}$ | 26 |
| 30 | 4-Cl | N | CO | H | $CH_3$ | —CO—$(CH_2)_2$—$CH_2Cl$ | 56–58 |
| 31 | 4-Cl | N | CO | H | $CH_3$ | —CO—cyclohexyl | 73 |
| 32 | 4-Cl | N | CO | H | $CH_3$ | —CO—$CH_2$—phenyl | 85 |
| 33 | 4-$\bigcirc$-Cl | CH | CO | H | $CH_3$ | CO—$C_9H_{19}$ | 72–75 |

What is claimed is:

1. A pharmaceutical composition for oral or parenteral use, free from pathogenic microorganisms which could be harmful to warm-blooded animals, comprising, as an active ingredient, an antimicotically effective amount of at least one compound of the formula

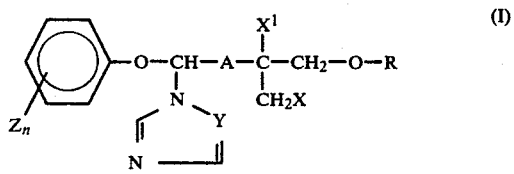

(I)

in which
R represents hydrogen, -CO-$R^1$ or -$SO_2$-$R^2$, wherein
$R^1$ represents a straight-chain or branched alkyl with 1 to 18 carbon atoms, which is unsubstituted or substituted by halogen, amino, acetylamino, alkoxy with 1 to 4 carbon atoms or by alkoxycarbonyl with 1 to 4 carbon atoms in the alkyl part; alkenyl or alkinyl with 2 to 6 carbon atoms; cycloalkyl with 5 to 7 carbon atoms; phenyl, phenylalkyl or phenoxyalkyl having in each case, 1 to 4 carbon atoms in the alkyl part and being unsubstituted or substituted in the phenyl part by halogen, amino, cyano, nitro or alkyl with 1 to 2 carbon atoms; alkylamino or dialkylamino with 1 to 4 carbon atoms in each alkyl part; or phenylamino which is unsubstituted or substituted by halogen, nitro or cyano;
$R^2$ represents straight-chain or branched alkyl with 1 to 4 carbon atoms; or phenyl group unsubstituted or substituted by halogen, amino, cyano, nitro or by alkyl with 1 to 2 carbon atoms;

A represents a keto group or a —CH(OH)— grouping,

X represents hydrogen or an —OR grouping, wherein R is as defined above, $X^1$ represents alkyl with 1 or 2 carbon atoms or phenyl which is unsubstituted or substituted by halogen, or alkyl with 1 to 2 carbon atoms;

Y represents —CH— or a nitrogen atom,

Z represents halogen; straight-chain or branched alkyl with 1 to 4 carbon atoms; cycloalkyl with 5 to 7 carbon atoms; halogenoalkyl with 1 or 2 carbon atoms and 1 to 5 halogen atoms; alkoxy or alkylthio with 1 or 2 carbon atoms in each case; alkoxycarbonyl with 1 to 5 carbon atoms; amino; cyano; nitro; phenyl or phenoxy each unsubstituted or substituted by halogen, amino, cyano, nitro or alkyl with 1 to 2 carbon atoms; phenylalkyl with 1 or 2 carbon atoms in the alkyl part, unsubstituted or substituted in the alkyl part by alkylcarbonyl with up to 3 carbon atoms and in the phenyl part by halogen, nitro or cyano; and n represents 0 or an integer from 1 to 5, or a salt thereof in admixture with a sterile pharmaceutical carrier.

2. A pharmaceutical composition as defined in claim 1 in the form of a sterile or isotonic aqueous solution.

3. A composition according to claim 1 containing from 0.5 to 95% of the said active compound by weight.

4. A medicament as defined in claim 1 in dosage unit form.

5. A medicament as defined in claim 1 in the form of a tablet, pill, dragee, capsule or ampoule.

6. A pharmaceutical composition of claim 1 wherein the active ingredient is 4-acetoxy-1-[4-(4'-chlorophenyl)phenoxy]-3,3-dimethyl-1(imidazol-1-yl)-butan-2-one.

* * * * *